(12) United States Patent
Long et al.

(10) Patent No.: US 9,398,838 B2
(45) Date of Patent: Jul. 26, 2016

(54) ENDOSCOPE

(75) Inventors: Gang Long, Wuhan (CN); Lei Song, Wuhan (CN); Zhiqiang Chen, Wuhan (CN); Yaohui Wu, Wuhan (CN); Ping Xia, Wuhan (CN)

(73) Assignee: WUHAN YOUCARE TECHNICAL CO., LTD., Wuhan (CN)

( * ) Notice: Subject to any disclaimer, the term of this patent is extended or adjusted under 35 U.S.C. 154(b) by 16 days.

(21) Appl. No.: 13/485,959

(22) Filed: Jun. 1, 2012

(65) Prior Publication Data

US 2012/0238819 A1 Sep. 20, 2012

Related U.S. Application Data

(63) Continuation-in-part of application No. PCT/CN2010/076974, filed on Sep. 16, 2010.

(30) Foreign Application Priority Data

| Dec. 2, 2009 | (CN) | 2009 1 0251256 |
| Dec. 15, 2009 | (CN) | 2009 1 0273215 |
| Aug. 30, 2010 | (CN) | 2010 1 0266551 |

(51) Int. Cl.
| A61B 1/00 | (2006.01) |
| A61B 1/005 | (2006.01) |
| A61B 1/307 | (2006.01) |
| A61B 1/303 | (2006.01) |
| A61B 1/313 | (2006.01) |

(52) U.S. Cl.
CPC ........... *A61B 1/00066* (2013.01); *A61B 1/0052* (2013.01); *A61B 1/00082* (2013.01); *A61B 1/303* (2013.01); *A61B 1/307* (2013.01); *A61B 1/313* (2013.01)

(58) Field of Classification Search
CPC .... A61B 1/012; A61B 1/3075; A61B 1/0105; A61B 1/0125; A61B 1/307
USPC ......... 600/135, 146, 149, 104, 114, 131, 434, 600/435, 523; 604/507–510
See application file for complete search history.

(56) References Cited

U.S. PATENT DOCUMENTS

| 2,584,619 | A | * | 2/1952 | Rubens et al. | 600/114 |
| 4,911,148 | A | * | 3/1990 | Sosnowski et al. | 600/136 |
| 5,287,845 | A | * | 2/1994 | Faul et al. | 600/135 |
| 5,855,549 | A | * | 1/1999 | Newman | 600/135 |
| 6,599,237 | B1 | * | 7/2003 | Singh | 600/114 |
| 2006/0149129 | A1 | * | 7/2006 | Watts et al. | 600/113 |

* cited by examiner

*Primary Examiner* — Anhtuan T Nguyen
*Assistant Examiner* — Timothy J Neal
(74) *Attorney, Agent, or Firm* — Matthias Scholl, PC; Matthias Scholl

(57) ABSTRACT

An endoscope including a catheter, a steering handle for controlling the bending of the catheter, and a pipe connector. The catheter includes an outer tube and an inner tube. The outer tube is sleeved outside the inner tube. The steering handle includes a handle sleeve and a handle cover. The handle sleeve is sleeved outside the handle cover. An axial guide rail and a sliding block are arranged between the handle sleeve and the handle cover. The guide rail and the sliding block are fixed on the handle sleeve or the handle cover respectively. The outer tube is fixedly connected with the handle sleeve. The inner tube penetrates a through hole in the center of the handle sleeve, is connected with a port of the pipe connector and fixed therein. The pipe connector is positioned in the handle cover and fixedly connected therewith.

16 Claims, 11 Drawing Sheets

ENDOSCOPE

CROSS-REFERENCE TO RELATED APPLICATIONS

This application is a continuation-in-part of International Patent Application No. PCT/CN2010/076974 with an international filing date of Sep. 16, 2010, designating the United States, now pending, and further claims priority benefits to Chinese Patent Application No. 200910251256.9 filed Dec. 2, 2009, to Chinese Patent Application No. 200910273215.X filed Dec. 15, 2009, and to Chinese Patent Application No. 201010266551.4 filed Aug. 30, 2010. The contents of all of the aforementioned applications, including any intervening amendments thereto, are incorporated herein by reference.

BACKGROUND OF THE INVENTION

1. Field of the Invention

The invention relates to the field of medical instruments, and more particularly to an endoscope.

2. Description of the Related Art

At present, there have been separate flexible ureteroscopes and rigid ureteroscopes in the world. The rigid ureteroscope is convenient to operate and can conveniently reach renal pelvis through the ureter, but because the front end of the rigid ureteroscope is inflexible, the rigid ureteroscope fails to adjust its direction to enter each group of renal calyces for conducting various methods of diagnosis and treatment after entering the renal pelvis. Although the front end of the flexible ureteroscope can be unidirectionally or multidirectionally bent and turn at a large angle, it's difficult for the flexible ureteroscope to enter the renal pelvis and renal calyces, and although the flexible ureteroscope can enter the renal pelvis and renal calyces under the guidance of X-rays, X-rays make greater damage to the body of doctors and patients. Developing a combined flexible and rigid ureteroscope has always been a goal pursued by the vast number of ureteroscope manufacturers and urologists.

The bending and steering of traditional endoscopes are generally controlled through a scissor type handle and a steering steel wire, thus the operation precision is low, the control of the steering angle is inaccurate, the visual angle is small, and the potential safety hazard is caused to the operation due to the technical bottlenecks of pipe size and blind angles.

SUMMARY OF THE INVENTION

In view of the above-described problems, it is one objective of the invention to provide an endoscope that has a simple operation and convenient steering.

To achieve the above objective, in accordance with one embodiment of the invention, there is provided an endoscope comprising a catheter, a steering handle for controlling the bending of the catheter, and a pipe connector, wherein the catheter comprises an outer tube and an inner tube, and the outer tube is sleeved outside the inner tube; the steering handle comprises a handle sleeve and a handle cover; the handle sleeve is sleeved outside the handle cover; an axial guide rail and a sliding block are arranged between the handle sleeve and the handle cover; the guide rail and the sliding block are fixed on the handle sleeve or the handle cover respectively; the outer tube is fixedly connected with the handle sleeve; the inner tube penetrates a through hole in the center of the handle sleeve, is connected with a port of the pipe connector and fixed therein; the pipe connector is positioned in the handle cover and fixedly connected therewith; and other ports of the pipe connector are connected with channel openings on the handle cover, respectively.

In a class of this embodiment, both the handle sleeve and handle cover are cylindrical.

In a class of this embodiment, the channel openings positioned on the handle cover comprise a fiber channel opening of the endoscope, a water-injection channel opening, and an instrument channel opening; the fiber channel opening of the endoscope is positioned in the center of one end of the handle cover, and the water-injection channel opening and the instrument channel opening are positioned at edge parts of the end of the handle cover respectively.

In a class of this embodiment, the guide rail is a strip-shaped chute axially arranged on the outer surface of the handle cover, the sliding block is a limit bolt arranged in a bolt hole on the side wall of the handle sleeve, and the bolt is matched with the chute.

In a class of this embodiment, a cervical plug for preventing fluid in a cavity from reversely flowing is arranged on the outer wall of a hard tube.

In a class of this embodiment, the cervical plug is a balloon arranged on the outer wall of the hard tube, and the balloon is connected with a charging connector through an inflation tube positioned on the outer wall of the hard tube.

In a class of this embodiment, the outer tube is a hard tube, the inner tube is an elbow tube, one end of the elbow tube is bent, the other end of the elbow tube is connected with a port of the pipe connector and fixed therein, and a guide wire or an optical fiber penetrates the elbow tube.

In a class of this embodiment, the outer tube is a hard tube, the inner tube is a soft tube; a steering channel and a working channel are arranged in the soft tube, a steering steel wire is arranged in the steering channel, a hard protective sleeve is arranged at the outer end of the soft tube, a positioning sleeve is arranged in the steering channel of the soft tube, an elastic tube is arranged in the soft tube between the positioning sleeve and the hard protective sleeve, the steering steel wire penetrates the positioning sleeve and the elastic tube, one end of the steering steel wire is fixedly connected with the hard protective sleeve, and the other end of the steering steel wire penetrates the port of the pipe connector to connect with a steering control valve positioned on the handle cover for controlling the stretching of the steering steel wire.

In a class of this embodiment, the working channel comprises an instrument channel, a fiber channel, and a water-injection channel, which are abreast arranged.

In a class of this embodiment, the steering channel arranged in the soft tube deviates from the central line of the soft tube.

Advantages of the invention are summarized below. The relative expansion and rotation between the outer tube and inner tube are achieved through the relative motion between the handle sleeve and the handle cover in the steering handle, and the axial expansion between the handle sleeve and the handle cover is achieved through the guide rail and the sliding block. After the sliding block retreats from the guide rail, the rotation between the handle sleeve and the handle cover can be achieved. During the rotating process, the inner tube penetrates the through hole in the center of the handle sleeve to connect with the channel openings fixed on the handle cover through the pipe connector and a flexible connecting pipe, and the outer tube is fixedly connected with the handle sleeve, so that the convenient expansion and rotation between the outer tube and the inner tube is achieved, and the work of the fiber channel opening of the endoscope, the water-injection channel opening, and the instrument channel opening is not affected.

The endoscope has a simple structure, convenient operation, and flexible steering, and can be used for tubal endoscopes, ureteroscopes, and the like.

DETAILED DESCRIPTION OF THE EMBODIMENTS

Example 1

Figure 1:
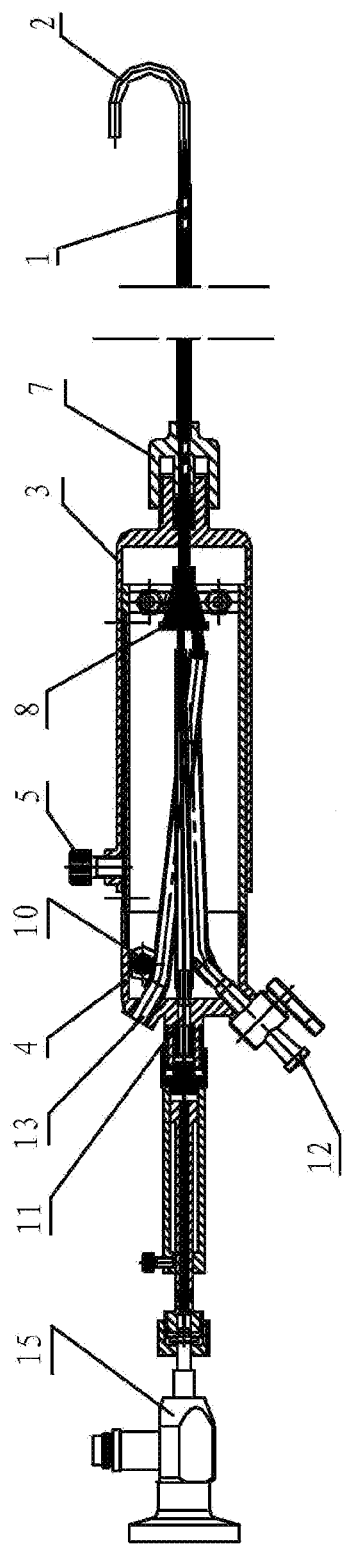
FIG. 1 is a structural diagram of an endoscope in accordance with one embodiment of the invention.
Figure 2:
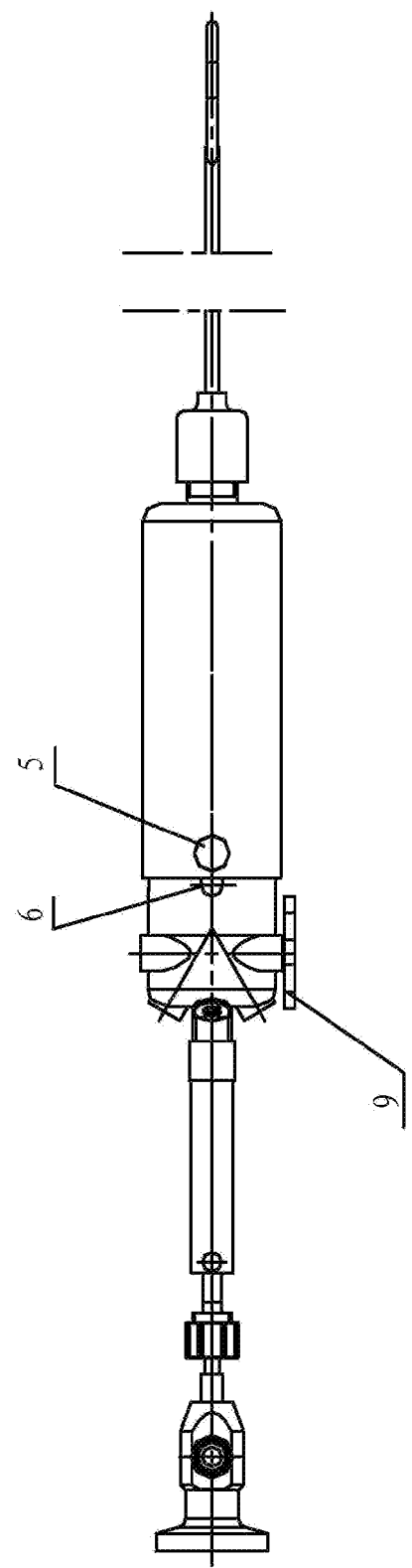
FIG. 2 is a top view of FIG. 1.

As shown in FIG. 1 and FIG. 2, a flexible endoscope comprises a catheter, a steering handle for controlling the bending of the catheter, and a pipe connector. The catheter comprises a hard tube 1 and a soft tube 2 which are made of plastic, and the hard tube 1 is sleeved outside the soft tube 2.

Figure 3:
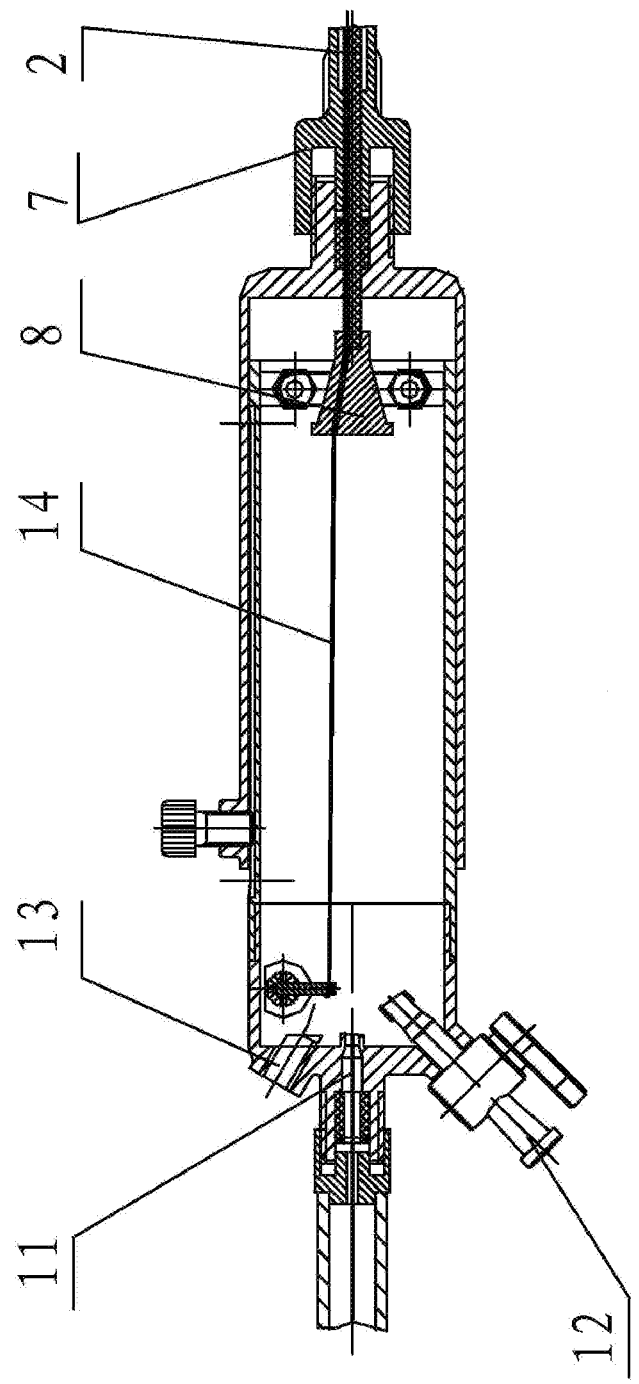
FIG. 3 is a structural diagram of a steering handle in accordance with one embodiment of the invention.
Figure 11:
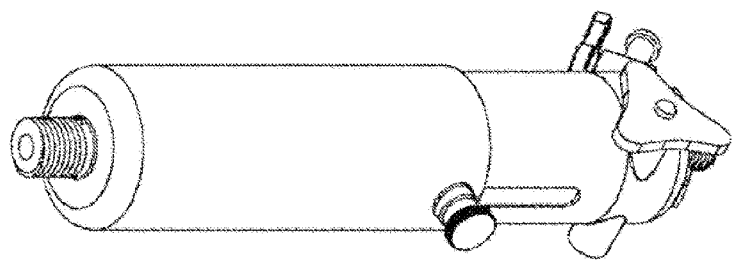
FIG. 11 is a three-dimensional diagram of a steering handle in accordance with one embodiment of the invention.

As shown in FIG. 3 and FIG. 11, the steering handle comprises a handle sleeve 3 and a handle cover 4. Both the handle sleeve and handle cover are cylindrical. The handle sleeve is sleeved outside the handle cover, and an axial guide rail and a sliding block are arranged between the handle sleeve and the handle cover. The guide rail is a strip-shaped chute 6 axially arranged on the outer surface of the handle cover. The sliding block is a limit blot 5 arranged in a bolt hole on the side wall of the handle sleeve, and the bolt 5 is matched with the chute 6.

The hard tube 1 is fixedly thread-connected with the handle sleeve 3 through a connecting flange 7. The soft tube 2 penetrates a through hole in the center of the handle sleeve 3, is connected with a port of the pipe connector 8 and fixed therein. A steering channel and a working channel are arranged in the soft tube 2. A steering steel wire 14 is arranged in the steering channel. The working channel comprises an instrument channel, a fiber channel, and a water-injection channel of the soft tube, which are abreast arranged.

Figure 4:
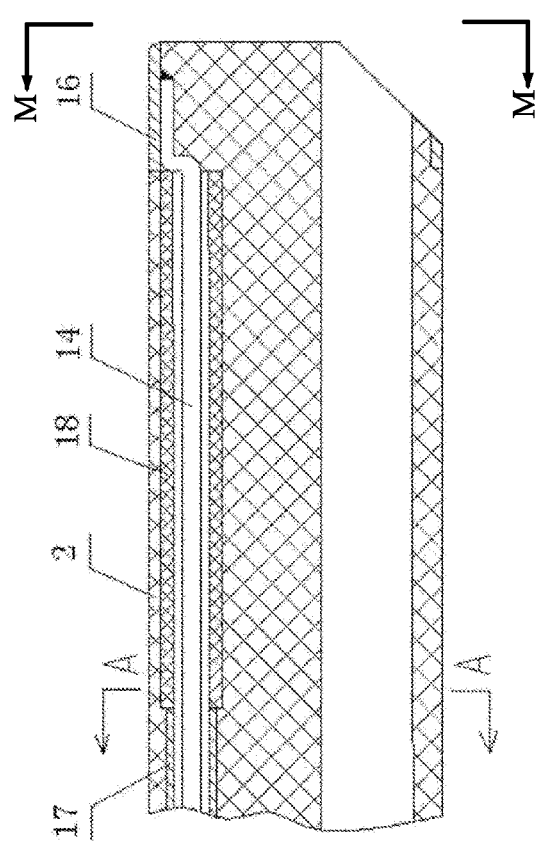
FIG. 4 is a cutaway view of a head of a soft tube in accordance with one embodiment of the invention.
Figure 5:
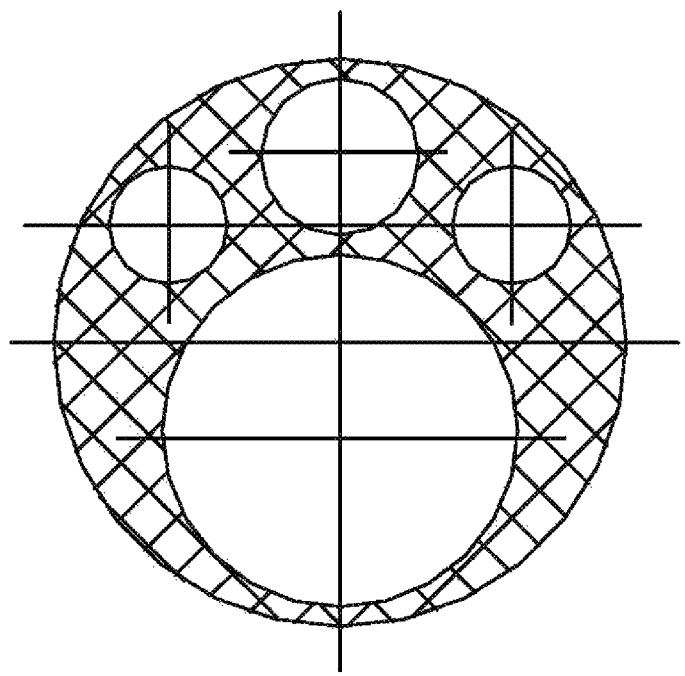
FIG. 5 is an A-A cutaway view of FIG. 4.
Figure 6:
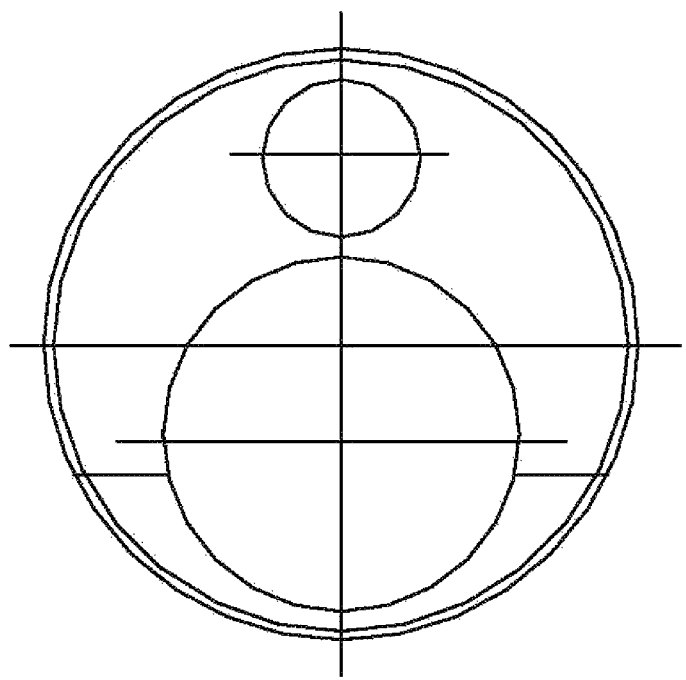
FIG. 6 is an M directional view of FIG. 4.

As shown in FIGS. 4-6, a ring-shaped hard protective sleeve 16 made of metal material is arranged at the outer end of the soft tube 2, sleeved outside the head of the soft tube, and molded into a whole with the soft tube by injection. An inclined surface (see FIG. 4) is arranged at the outer end of the soft tube 2, so as to facilitate the head of the soft tube to extend in the organ. A positioning sleeve 17 is arranged in the steering channel of the soft tube and adopts a stainless steel pipe. An elastic tube 18 made of polymer material is arranged in the soft tube between the positioning sleeve 17 and the hard protective sleeve 16, one end of the elastic tube 18 is in contact with the positioning sleeve, and the other end of the elastic tube 18 is in contact with the hard protective sleeve. The steering steel wire 14 penetrates the positioning sleeve and the elastic tube, one end of the steering steel wire 14 is fixedly connected with the hard protective sleeve, and the other end of the steering steel wire 14 penetrates the port of the pipe connector 8 to connect with a steering control valve positioned on the handle cover for controlling the stretching of the steering steel wire 14. The steering control valve is a rotary handle 9. A rotating shaft of the rotary handle 9 is installed on the handle cover. A rotating wheel 10 is installed on the rotating shaft and positioned in the handle cover. The steering steel wire 14 is fixed on the rotating wheel 10.

Channel openings positioned on the handle cover comprise a fiber channel opening 11 of the endoscope, a water-injection channel opening 12 of the soft tube, and an instrument channel opening 13. The fiber channel opening 11 of the endoscope is positioned in the center of the end of the handle cover, and an endoscope fiber 15 extends from the fiber channel opening 11 of the endoscope and extends out from the head of the soft tube 2. The water-injection channel opening and the instrument channel opening are positioned at the edge parts of the end of the handle cover respectively, and communicated with a water-injection channel and an instrument channel in the soft tube through the pipe connector 8.

The pipe connector 8 is a four-way pipe, positioned in the handle cover and fixedly connected with the handle cover through a bolt. A port at one end of the pipe connector 8 is connected with the soft tube, and the outer ends of ports at the other end of the pipe connector 8 are connected with the fiber channel opening 11 of the endoscope, the water-injection channel opening 12 of the soft tube, and the instrument channel opening 13 on the handle bocy cover through corresponding flexible connecting pipes; the inner ends are connected with the instrument channel, the fiber channel, and the water-injection channel in the soft tube 2, respectively.

The three working channels in the soft tube have different specifications in the size according to different demands. The angle at the front end of the soft tube is controlled directly through the steering handle and the steering control valve. when the rotary handle of the steering control valve rotates, the steering steel wire is driven to retract, and the front end of the soft tube is pulled to turn, see FIG. 1. After the rotary handle is loosened, the elastic tube returns, so that the whole soft tube returns. The bending process is simple to operate, the steering angle can be accurately controlled, the angle of steering and bending of the soft tube is determined according to the length of the elastic tube, and can reach 180 degrees or above. The full-range direction changing (including bending direction and angle) and expansion can be realized during the whole bending process with the stretching motion and rotary motion between the soft tube and the hard tube, the visual angle can reach 360 degrees, and the blind angle is thoroughly eliminated.

Several regular applications are listed as follows:

1. The application in urinary surgery: the endoscope is used in combination with a ureter hard tube and various instruments to form a ureterorenoscope. The ureterorenoscope can be used not only for observing the ureter, bladder, renal pelvis, and renal calyces, but also for taking biopsies, removing foreign bodies and calculus, removing small tumors, performing coagulation bleeding, and performing urethrotomy, thereby becoming an important method for diagnosing and treating upper urinary diseases.

2. The application in neurosurgery: the endoscope is used in combination with a hard tube, and after possessing all the advantages of the conventional hard endoscopes and flexible endoscopes, the multi-channel soft tube can be widely used in treatment of hydrocephalus, intraventricular or periventricular lesions, skull base surgery, pituitary tumors, aneurysm, and intracranial hematoma, particularly used for septated subdural hematoma treatment and percutaneous endoscopic lumbar discectomy, and even can be used for intra-axial brain tumor biopsy, excision of small tumors, microvascular decompression for trigeminal neuralgia, vestibular neurectomy, etc.

3. The application in gynecology: the endoscope can be combined with a hard tube to be used as a tubal endoscope, or used to optimize the existing hysteroscope, laparoscope, and vaginoscope. The endoscope is used in patients with clinical cervical precancerous lesion or cervical cancer suspect patients, patients who have abnormal cells discovered in cancer-prevention pictures, and patients with cervical lesions after follow-up treatment for grasping the treatment effect, and checking whether the lesions recur or another lesions appear, and the abnormal uterine bleeding recurs, such as intrauterine fibroids, polyp and endometrial carcinoma, abnormal ultrasonic image finding, infertility and birth control complication, physical or special change of endometrium due to hormone replacement and the application of tamoxifen, and previous IVF (in-vitro fertilization) failure, is used for replacing the hysteroscope for inspecting the conditions of endometrium and habitual abortion, viewing the deformity and adhesion of the uterine cavity and inspecting the foreign body in the uterine cavity, and used for removing the gynecology benign tumors, diagnosing and treating the ectopic pregnancy, as well as treating the ovarian cyst, pelvic stripping adhesion, endometriosis by cautery and tubal ligation.

Besides, the endoscope can be used in digestion internal medicine department, pancreas surgery, vascular surgery, respiratory department, etc.

Example 2

Figure 7:
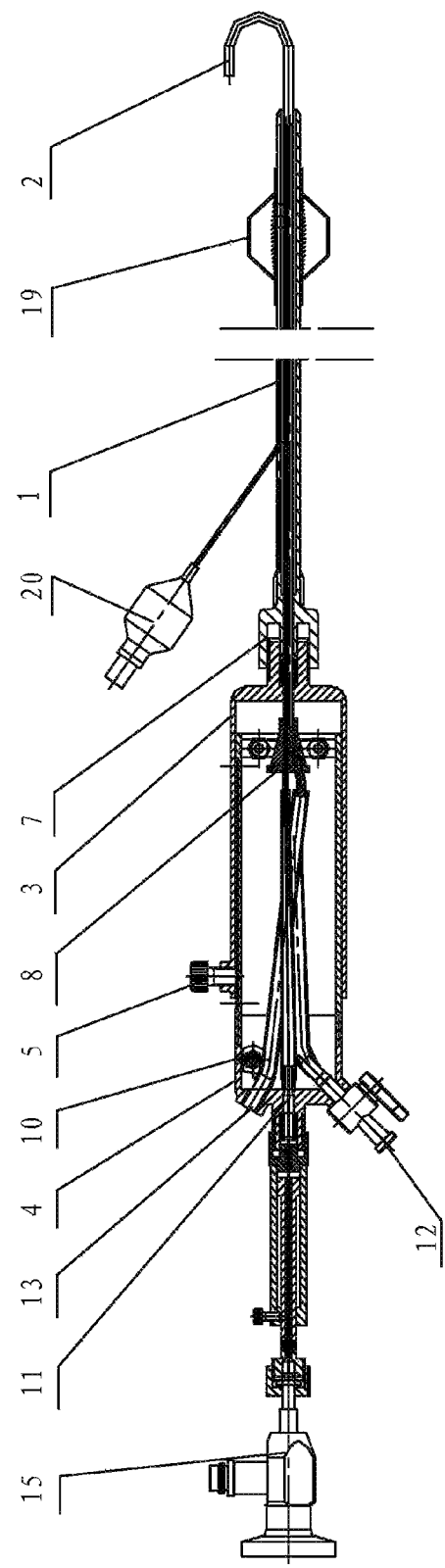
FIG. 7 is a structural diagram of an endoscope in accordance with another embodiment of the invention.
Figure 8:
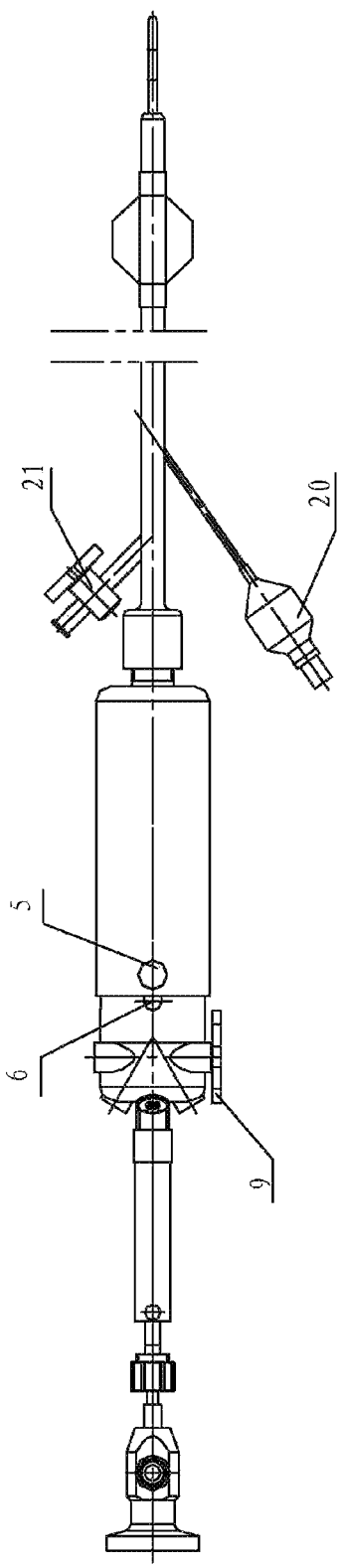
FIG. 8 is a top view of FIG. 7.
Figure 9:
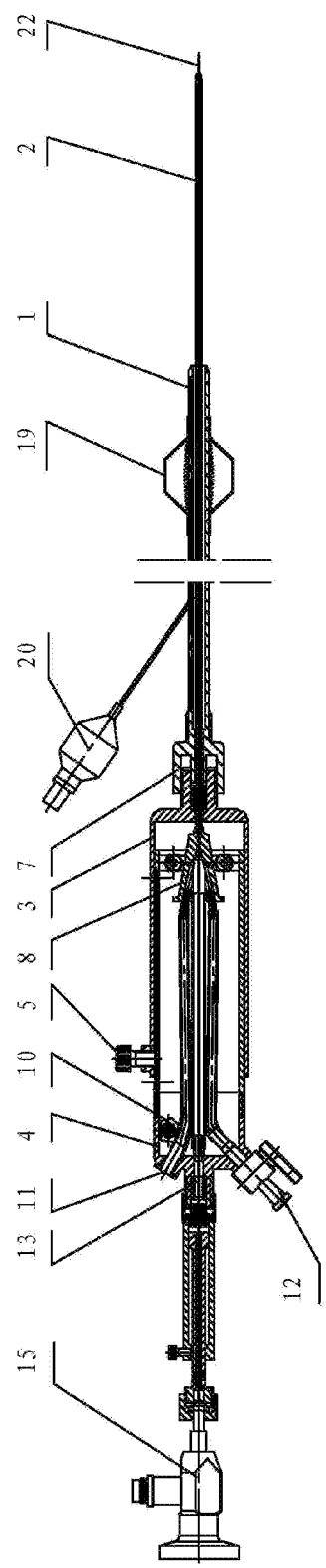
FIG. 9 is a structural diagram of an endoscope in accordance with another embodiment of the invention.
Figure 10:
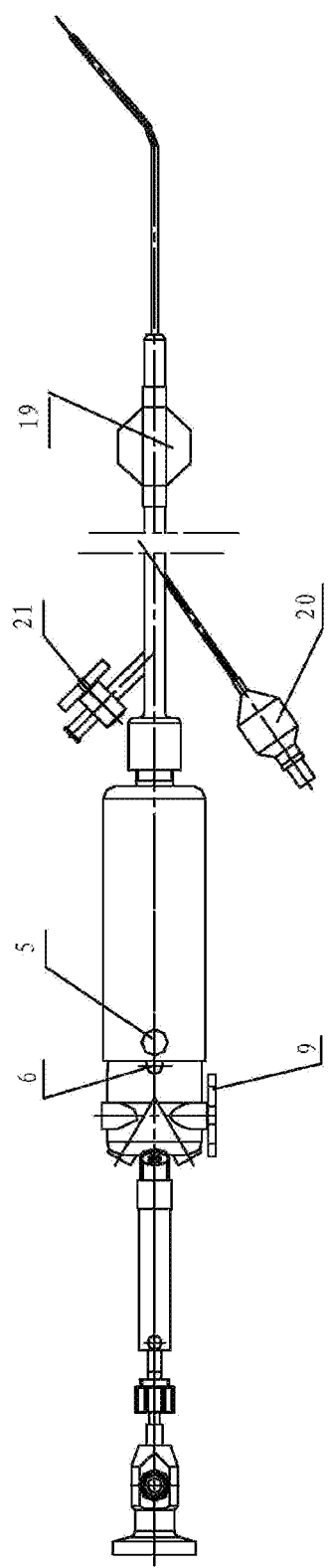
FIG. 10 is a top view of FIG. 9.

As shown in FIG. 7 and FIG. 8, the example is basically the same as Example 1, except that a balloon 19 for preventing fluid in a cavity from reversely flowing and a water-injection channel opening 21 of the hard tube are arranged on the outer wall of the hard tube. The balloon 19 is connected with a charging connector 20 through an inflation tube positioned on the outer wall of the hard tube. The balloon is not inflated when in use, but inflated after being inserted in the cavity. The water-injection channel opening 21 of the hard tube is used for injecting water into the cavity through the hard tube 1.

Example 3

The example is basically the same as Example 1, except that the outer tube 1 is a guide tube, the inner tube 2 is an elbow tube, one end of the elbow tube is bent, the other end of the elbow tube is connected with a port of the pipe connector 8 and fixed therein, and a guide wire or an optical fiber penetrates the elbow tube. The guide wire 22 is made of stainless steel material, and the diameter of the guide wire 22 ranges from 0.015 mm to 0.35 mm. The outer end of the elbow tube is bent, and the bent end of the elbow tube is made of material softer than that of other parts of the elbow tube. The guide tube is made of polypropylene.

A balloon 19 for preventing the fluid in the cavity from reversely flowing and a water-injection channel opening 21 of the hard tube are arranged on the outer wall of the guide tube. The balloon 19 is connected with a charging connector 20 through an inflation tube positioned on the outer wall of the guide tube. The balloon 19 is not inflated when in use, but inflated after being inserted in the cavity.

According to the demands of actual conditions, three operation schemes can be adopted during the operation, which are described as follows.

Method 1: Applying the Guide Wire after Applying an Image and Lighting Fiber

The guide tube enters via the vaginal orifice of a patient, and then is placed in the genital tract of the patient, so as to achieve the effect of vaginal dilation. The elbow tube is inserted into the guide tube, and the front end of the elbow tube reaches or enters the fallopian tube orifice at the bottom of uterus with the help of the guide tube, so as to provide support for the later water injection or instrument dredging. The image and lighting fiber penetrates the fiber channel and elbow tube, and the guide wire directly penetrates the elbow tube, reaches the isthmus after directly passing through the tubal interstitial portion under the guidance of the guide tube, and even can reach the ampullar region. In use, the state of illness can be observed through the image and lighting fiber during the water injection. The image and lighting fiber is connected with a camera system, and the related gynecologic operation can be completely finished under the endoscope with diameter smaller than that of the hysteroscope through an imaging system with 20,000 pixels.

Method 2: Only Applying the Guide Wire

After the observation and diagnosis through the image and lighting fiber, the image and lighting fiber is taken out, the guide wire penetrates the guide wire channel and elbow tube. Thus, those seriously-blocked fallopian tubes or thinner fallopian tubes through which the image and lighting fiber fail to enter are dredged directly with the guide wire under the condition of water injection failure. The guide tube guides the elbow tube to reach uterus through the cervix opening, the elbow tube guides the guide wire 3 to reach the tubal interstitial portion through the fallopian tube orifice, and the blocked fallopian tube can be directly dredged. The method should be completed under X-rays by virtue of contrast medium.

Method 3: Taking the Image and Lighting Fiber Out, and Applying an Instrument/Laser Fiber (without a Guide Wire)

The guide wire 22 is not provided in this method. After the observation and diagnosis through the image and lighting fiber, the image and lighting fiber is taken out, an instrument or a laser fiber is introduced, laser is marked for dredging, and the guide wire is not introduced at the moment.

During the practical operation, the uterine cavity can be reached through the instrument channel for the hysteroscope, and the fallopian tube is reached after distention through a hysteroscopy pump.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. An endoscope, comprising:
a catheter comprising a hard tube and a soft tube, said hard tube having a first outer wall;
a steering handle assembly comprising a tubular handle sleeve, a rotary handle, and a tubular handle base, said rotary handle comprising a rotating shaft, and said tubular handle base having a second outer wall; and
a pipe connector;
wherein:
said soft tube comprises a distal end adapted to interface with a patient's body, a proximal end, and a plurality of channels extending from said distal end to said proximal end;
one of said plurality of channels accommodates a steering steel wire, and said steering steel wire is connected to said distal end;
said steering handle assembly is adapted to stretch said steering steel wire, whereby said steering steel wire bends said distal end;
said hard tube is movably sleeved on said soft tube;
said soft tube is adapted to extend out of said hard tube, to retract into said hard tube, and to rotate about said hard tube;
said tubular handle sleeve is sleeved on said tubular handle base;
a guiding groove is axially disposed on said second outer wall;
a sliding block is disposed on said tubular handle sleeve, and said sliding block is adapted to slide along said guiding groove;
said tubular handle sleeve is adapted to move axially about said tubular handle base by sliding said sliding block along said guiding groove;
said tubular handle sleeve controls said soft tube to extend out of said hard tube or to retract into said hard tube when said tubular handle sleeve moves axially about said tubular handle base;
said tubular handle sleeve is adapted to rotate about said tubular handle base;
said rotating shaft is disposed on said tubular handle base;
a rotating wheel is disposed on said rotating shaft and in said tubular handle base;
said steering steel wire is fixed on said rotating wheel;
said rotating wheel stretches said steering steel wire and bends said distal end when said rotary handle rotates about said rotating shaft;
said hard tube is fixedly connected to said tubular handle sleeve;
said pipe connector is positioned in said tubular handle base and is fixedly connected to said tubular handle base;
said proximal end is fixedly connected to said pipe connector;
said pipe connector comprises a plurality of first ports for communicating with said plurality of channels; and
said tubular handle base comprises a plurality of second ports for communicating with said plurality of first ports.

2. The endoscope of claim 1, wherein:
said plurality of second ports comprises a fiber channel opening, a water-injection channel opening, and an instrument channel opening;
said fiber channel opening is positioned in a center of one end of said tubular handle base; and
said water-injection channel opening and said instrument channel opening are positioned at edge parts of the end of said tubular handle base, respectively.

3. The endoscope of claim 1, wherein:
said sliding block is a bolt arranged in a bolt hole on a side wall of said tubular handle sleeve; and
said bolt is matched with said guiding groove.

4. The endoscope of claim 3, wherein when in use, when said bolt is screwed out of said guiding groove, said tubular handle sleeve is rotatable with respect to said tubular handle base and said hard tube is rotatable with respect to said soft tube.

5. The endoscope of claim 1, wherein a cervical plug for preventing fluid in a cavity from reversely flowing is arranged on said first outer wall.

6. The endoscope of claim 5, wherein said cervical plug is a balloon arranged on said first outer wall, and said balloon is connected with a charging connector through an inflation tube positioned on said first outer wall.

7. The endoscope of claim 6, wherein:
said soft tube is an elbow tube;
said distal end is bent; and
a guide wire or an optical fiber extends through said elbow tube.

8. The endoscope of claim 6, wherein
a steering channel and a working channel are arranged in said soft tube;
said steering steel wire is arranged in said steering channel;
a hard protective sleeve is sleeved on said soft tube;
a positioning sleeve is arranged in said steering channel;
an elastic tube is arranged in said soft tube between said positioning sleeve and said hard protective sleeve;
said steering steel wire extends through said positioning sleeve and said elastic tube; and
one end of said steering steel wire is fixedly connected with said hard protective sleeve, and the other end of said steering steel wire passes through one of said plurality of first ports to connect with said rotary handle.

9. The endoscope of claim 8, wherein said working channel comprises an instrument channel, a fiber channel, and a water-injection channel, which are abreast arranged.

10. The endoscope of claim 8, wherein said steering channel deviates from the central line of said soft tube.

11. The endoscope of claim 1, wherein:
said soft tube is an elbow tube;
said distal end is bent; and
a guide wire or an optical fiber extends through said elbow tube.

12. The endoscope of claim 1, wherein:
a steering channel and a working channel are arranged in said soft tube;
said steering steel wire is arranged in said steering channel;
a hard protective sleeve is sleeved on said soft tube;
a positioning sleeve is arranged in said steering channel;
an elastic tube is arranged in said soft tube between said positioning sleeve and said hard protective sleeve;
said steering steel wire extends through said positioning sleeve and said elastic tube; and
one end of said steering steel wire is fixedly connected with said hard protective sleeve, and the other end of said steering steel wire passes through one of said plurality of first ports to connect with said rotary handle.

13. The endoscope of claim 12, wherein said working channel comprises an instrument channel, a fiber channel, and a water-injection channel, which are abreast arranged.

14. The endoscope of claim 12, wherein said steering channel deviates from the central line of said soft tube.

15. The endoscope of claim 1, wherein when in use, a movement of said hard tube with respect to said soft tube is transferred by a movement of said tubular handle sleeve with respect to said tubular handle base.

16. The endoscope of claim 1, wherein when in use, an axial movement of said hard tube with respect to said soft tube is transferred by an axial movement of said tubular handle sleeve with respect to said tubular handle base via sliding said sliding block along said guiding groove.

\* \* \* \* \*